United States Patent [19]

de Troostembergh et al.

[11] Patent Number: 5,480,785
[45] Date of Patent: Jan. 2, 1996

[54] PRODUCTION OF XANTHAN GUM BY FERMENTING A FEEDSTOCK CONTAINING A MIXTURE OF MANNOSE AND GLUCOSE

[75] Inventors: Jean-Claude M. G. de Troostembergh, Houwaart; Roland H. F. Beck; Bénédicte L. T. De Wannemaeker, both of Brussels, all of Belgium

[73] Assignee: Cerestar Holding B.V., Sas van Gent, Netherlands

[21] Appl. No.: 183,938

[22] Filed: Jan. 21, 1994

[30] Foreign Application Priority Data

Jan. 30, 1993 [GB] United Kingdom ............... 9301894

[51] Int. Cl.$^6$ ............... C12P 19/06; C08B 37/00
[52] U.S. Cl. ............... 435/104; 536/114; 536/123; 536/126
[58] Field of Search ............... 435/104; 536/114, 536/123, 126

[56] References Cited

U.S. PATENT DOCUMENTS

| | | | |
|---|---|---|---|
| 3,020,207 | 2/1962 | Patton | 435/104 |
| 3,119,812 | 1/1964 | Rogovin et al. | 435/104 |
| 3,256,271 | 6/1966 | Schweiger | 435/104 |
| 4,083,881 | 4/1978 | Takemura et al. | 568/863 |
| 4,418,145 | 11/1983 | Weisrock | 435/104 |
| 4,713,449 | 12/1987 | Vanderslice et al. | 536/123 |
| 4,868,293 | 9/1989 | Vanderslice | 536/123 |
| 5,102,561 | 9/1989 | Vanderslice | 252/8.554 |

FOREIGN PATENT DOCUMENTS

| | | |
|---|---|---|
| 0046007 | 7/1982 | European Pat. Off. . |
| 0211288 | 9/1987 | European Pat. Off. . |

OTHER PUBLICATIONS

Baig et al, "Microbial Synthesis of Xanthan Gum . . . ," Pakistan J. Sci. Ind. Res. 25(4):134–138 (1982).

*Primary Examiner*—David M. Naff
*Assistant Examiner*—Francisco C. Prats
*Attorney, Agent, or Firm*—Cushman Darby & Cushman

[57] ABSTRACT

A process of producing xanthan gum using a Xanthomonas microorganism is provided. Increased yields of xanthan gum are obtained by using mannose as part of the carbohydrate component of the fermentation feedstock. Preferably, the carbohydrate component of the feedstock is a mixture of mannose and glucose. More preferable is a mixture comprising 5 to 60% by weight mannose, particularly 20 to 45% by weight mannose, the balance being glucose although minor amounts of other sugars, e.g. maltose, may also be present. The carbohydrate component of the feedstock may be in the form of a raffinate stream from a glucose epimerization.

6 Claims, No Drawings

PRODUCTION OF XANTHAN GUM BY FERMENTING A FEEDSTOCK CONTAINING A MIXTURE OF MANNOSE AND GLUCOSE

The present invention relates to a feedstock for a fermentation particularly to a feedstock comprising mannose and more particularly to the use of such a feedstock in a fermentation process for the production of xanthan gum.

In the past fifty years fermentation processes have become of increasing significance for the production of complex organic molecules not capable of synthesis on an industrial scale by other means. Although the classical fermentation processes have been known and used for centuries to produce simple products such as ethanol and acetic acid it is only relatively recently that microbial fermentation processes have been developed to produce more complex products for the food, chemical and pharmaceutical industries.

A typical fermentation process involves the cultivation of a specialist microorganism on a suitable feedstock whereby the organism increases in number and at the same time or subsequently produces metabolites some or all of which are desired products of the process. An example is the growth of *Xanthomonas campestris* on a suitable medium so as to produce the desired metabolite xanthan gum. Xanthan gum is a complex polysaccharide containing D-glucose, D-mannose and D-glucuronic acid which has excellent rheological properties for applications in the food, pharmaceutical and chemical industries.

More recently, the range of microbial fermentation processes has been extended by use of genetically engineered microorganisms and, additionally, fermentation processes have been devised in which the enzymes responsible for the fermentation are provided by a culture of animal cells, for example in the production of glycoproteins such as the human antihaemophilic Factor VIII.

The feedstock for a microbial or cell culture fermentation process generally comprises a carbohydrate, a source of nitrogen and various minerals. The carbohydrate may be a complex substance such as starch or a maltodextrin which a microorganism for example can break down to simple sugars before utilizing such sugars in its metabolic processes. More frequently however the fermentation feedstock is made up directly from a simple sugar such as maltose or, more usually, glucose. It is for example conventional practice to use glucose as the carbohydrate component in the *Xanthomonas campestris* fermentation referred to above. We have now found that in certain fermentation processes in which, as in xanthan gum, the desired product comprises mannose units, increased yields of the desired metabolite may be obtained by using mannose as part of the carbohydrate component of the fermentation feedstock. Mannose is an epimer of glucose but is less readily available and hence more expensive than glucose. Despite the increased cost of mannose however we have found that it may be economic to replace part of the glucose conventionally used in a fermentation particularly if the replacement is a less expensive mixture of mannose and glucose as hereinafter described because the increased yield of the, usually, high value product more than compensates for any increased cost of the feedstock. All references to mannose in this specification are to D-mannose.

Accordingly, the invention comprises a fermentation process for the production of a product comprising mannose units in which a simple sugar is a component of the fermentation feedstock and which is characterized in that part of the sugar is mannose.

Preferably the sugar component of the fermentation feedstock is a mixture of mannose and glucose, more preferably a mixture comprising 5 to 60% by weight mannose, particularly 20 to 45% by weight mannose, the balance being mainly glucose although minor amounts of other sugars eg. maltose may also be present. Mannose may be produced by the epimerization of glucose in the presence of a catalyst eg. a molybdenum compound. The product of this epimerization reaction is a mixture of mannose and glucose, typically containing about 30% by weight mannose and it is this mixture in particular which may be used as such as a fermentation feedstock according to the present invention. It is also possible to use a glucose syrup as the epimerization feedstock eg. a mixture of 90% or more glucose with glucose oligomers such as maltose in which case the fermentation feedstock will also contain small amounts of the glucose oligomers. The epimerization product may also be treated, eg chromatographically, in order to separate mannose and a co-product raffinate stream comprising glucose and mannose. Such a raffinate stream may comprise 5 to 15% by weight mannose and may also be used as feedstock in a process according to the present invention. Alternatively, if a desired fermentation product is relatively rich in mannose units it is possible to add mannose to the epimerization product or to enrich the product chromatographically to produce a suitable fermentation feedstock. The use of mannose/glucose mixtures is particularly useful for the production of a fermentation product comprising both mannose and glucose units.

The fermentation feedstock according to the invention is especially useful in the production of xanthan gum by a fermentation process particularly when the organism used is *Xanthomonas campestris*. As is shown in the Examples which follow in this specification, replacement of part of the glucose in such a fermentation by an equivalent amount of mannose can give an improvement in yield of xanthan gum of more than 30% by weight.

The fermentation process according to the invention may be carried out batchwise, in which case all of the feedstock is added at the start of the fermentation, or semi-continuously, in which the feedstock is added progressively throughout the fermentation, the mannose and another simple sugar such as glucose being added either or separately or, preferably, together.

The invention will now be further described and illustrated by reference to the following Examples.

EXAMPLES 1 to 4

In the following fermentations the organism used was *Xanthomonas campestris* NRRL 1459-14 (LMG 574) type t1.

A pre-culture medium was used to prepare the innoculum for the fermentation. This medium had the following composition:

(all percentages in these Examples being by weight)

| | |
|---|---|
| Malt extract | 0.3% |
| Yeast extract | 0.3% |
| Bacto-peptone (nitrogen source) | 0.5% |
| Dipotassium hydrogen phosphate | 0.5% |
| Magnesium sulphate | 0.02 % |

The solution was adjusted to pH 7 by addition of sulphuric acid before being sterilized by heating at 120° C. for 20 minutes A 20% carbohydrate stock solution which was separately sterilized by heating at 120° C. for 20 minutes was added to the above solution as a 2% solution of either:

Glucose or A mixture of 30% mannose and 70% glucose 100 mls of the pre-culture media thus prepared were inoculated with the *Xanthomonas campestris* organism from a Revco tube and incubated at 28° C. on a rotary table for 2 days.

The fermentation medium used in the Examples comprised:

| | |
|---|---|
| Malt extract | 0.3% |
| Yeast extract | 0.3% |
| Bacto-peptone | 0.5% |
| Potassium dihydrogen phosphate | 0.5% |
| Magnesium sulphate | 0.02% |

This solution was adjusted to pH 7 before sterilization.

The carbohydrate components of the fermentation medium were glucose or a 30% mannose/70% glucose mixture. The glucose or glucose/mannose mixture was dissolved in 100 mls water to give concentrations of 1%, 1.5%, 2% and 3% respectively.

The fermenter had a 2 liter capacity and contained 1.3 liter of the sterilized medium described above plus, 100 mls of the glucose or mannose/glucose solution plus 100 mls of the pre-culture innoculum. The temperature was maintained at 29° C., the rate of aeration was 1.5 vvm (3 liters per minute) and the agitation rate was 850 rpm.

Each fermentation was allowed to continue for 18 hours after which time the amount of xanthan gum produced was determined and the amount of residual sugars measured. The determination of xanthan gum was carried out by diluting the fermentation medium with three times its volume of isopropanol and filtering off the precipitated xanthan gum. After washing the precipitate with two volumes of isopropanol, filtering and drying in an oven at 40° C. overnight the xanthan gum was weighed.

Residual sugars were determined by high pressure liquid chromatography of the medium after precipitation of the xanthan gum and evaporation of the isopropanol.

The results of the fermentations were as follows:

| Example | Sugar(s) | Sugar(s) concentration | Xanthan concentration g/liter | Xanthan yield on sugar(s) consumed | Xanthan yield on total sugar(s) |
|---|---|---|---|---|---|
| 1(a) | glucose | 1% | 10.4 | 104 | 104 |
| 1(b) | mannose/glucose | 1% | 11.6 | 119 | 116 |
| 2(a) | glucose | 1.5% | 11.7 | 87 | 78 |
| 2(b) | mannose/glucose | 1.5% | 14.0 | 102 | 93 |
| 3(a) | glucose | 2.0% | 13.6 | | 68 |
| 3(b) | mannose/glucose | 2.0% | 14.5 | 91 | 72 |
| 4(a) | glucose | 3.0% | 10.4 | | 35 |
| 4(b) | mannose/glucose | 3.0% | 13.9 | 88 | 46 |

As can be seen from the results increases in yield were obtained in all the four comparative pairs of experiments for the mannose/glucose mixture compared with glucose alone, the highest percentage increase being 34% in Example 4.

EXAMPLES 5 and 6

As in Examples 1 to 4 the organism used was *Xanthomonas campestris* NRLL 1459-14 (LMG 574) type t1.

A pre-culture medium was used to prepare the innoculum for the fermentation. This medium had the following composition (all percentages in these Examples being by weight):

| | |
|---|---|
| Malt extract | 0.3% |
| Yeast extract | 0.3% |
| Bacto-peptone (nitrogen source) | 0.5% |
| Dipotassium hydrogen phosphate | 0.5% |
| Magnesium sulphate | 0.02% |

The solution was adjusted to pH 7 by addition of sulphuric acid before being sterilized by heating at 120° C. for 20 minutes.

A 20% carbohydrate stock solution which was separately sterilised by heating at 120° C. for 20 minutes was added to the above solution as a 2% solution of glucose.

100 mls of the pre-culture media thus prepared were inoculated with the *Xanthomonas campestris* organism from a Petri plate and incubated at 28° C. on a rotary table for 4 days. The fermentation medium used in the Examples comprised:

| | |
|---|---|
| Ammonium nitrate | 1.144 g/l |
| Potassium dihydrogenphosphate | 2.866 g/l |
| Magnesium chloride | 0.507 g/l |
| Sodium sulphate | 0.089 g/l |
| Citric acid monohydrate | 2.3 g/l |
| Boric acid | 0.006 g/l |
| Ferric chloride | 0.024 g/l |
| Calcium carbonate | 0.020 g/l |
| Zinc chloride | 0.030 g/l |
| Concentrated hydrochloric acid | 0.13 ml |

This solution was adjusted to pH 7 with 5N sodium hydroxide solution before sterilisation.

The carbohydrate components of the fermentation medium were glucose or a 30% mannose/70% glucose mixture. The glucose or glucose/mannose mixture was dissolved in 100 mls water to give a concentration of 3%.

The fermenter had a 2 liter capacity and contained 1.3 liter of sterilized medium described above plus 100 mls of the glucose or mannose/glucose solution plus 100 mls of the pre-culture innoculum. The temperature was maintained at 29° C., the rate of aeration was 1.5 vvm (3 liters per minute) and the agitation rate was 850 rpm. During the fermentations the pH was controlled at 7 by the addition of a 2N aqueous solution of potassium hydroxide. After 6.6 days fermentation when all the sugars had been consumed the xanthan gum produced, was determined by diluting the fermentation medium with three times its volume of isopropanol and filtering off the precipitated xanthan gum. After washing the precipitate with two volumes of isopropanol, filtering and drying in an oven at 40° C. ovenight the xanthan gum was weighed.

The results of the fermentation were as follows:

| Example | Sugar(s) | Xanthan concentration g/l | Xanthan yield on total sugar(s) | Yield Stress* Pa |
| --- | --- | --- | --- | --- |
| 5(a) | glucose | 9.78 | 32 | 20.5 |
| 5(b) | glucose/mannose | 10.97 | 36 | 21.5 |
| 6(a) | glucose | 10.5 | 35 | 18.5 |
| 6(b) | glucose/mannose | 14.4 | 48 | 17.5 |

*Yield stress is measured at 20° C. by a Bohlin CS Rheometer using a 3% aqueous xanthan solution containing 0.1% sodium chloride.

We claim:

1. In a process for the production of xanthan gum which comprises fermenting a feedstock in the presence of a Xanthomonos microorganism which is effective to ferment said feedstock and form xanthan gum, the improvement in which the fermentation feedstock comprises a mixture of mannose and glucose, said mixture comprising 5 to 60% by weight mannose, the balance being glucose.

2. A process as set forth in claim 1 in which the feedstock contains a minor amount of at least one other sugar.

3. A process as set forth in claim 1 in which the mixture of mannose and glucose is the product obtained by the epimerization of glucose.

4. A process as set forth in claim 3 in which the feedstock is a raffinate stream from a glucose epimerization and contains 5 to 15% mannose.

5. A process as set forth in claim 1 in which the microorganism is *Xanthomonas campestris*.

6. A process for producing xanthan gum which comprises the step of fermenting a feedstock in the presence of a Xanthemonas microorganism which is effective to ferment said feedstock and form xanthan gum, wherein the fermentation feedstock comprises a mixture of mannose and glucose, said mixture comprising 20 to 45% by weight of mannose, the balance being glucose.

* * * * *